United States Patent [19]

Sestak et al.

[11] Patent Number: 4,539,929
[45] Date of Patent: Sep. 10, 1985

[54] TEMPERATURE SENSITIVE RECLOSURE INDICATOR

[75] Inventors: Joseph T. Sestak; Dennis C. Coon, both of Erie, Pa.

[73] Assignee: American Sterilizer Company, Erie, Pa.

[21] Appl. No.: 546,313

[22] Filed: Oct. 28, 1983

[51] Int. Cl.³ .............................................. G01K 1/02
[52] U.S. Cl. .................................... 116/221; 116/216; 126/388; 292/DIG. 66
[58] Field of Search .................... 116/2, 85, 101, 216, 116/221; 374/205; 337/343, 348, 376; 340/594; 126/388; 422/58, 118, 119; 436/1; 292/92, DIG. 66; 49/2

[56] References Cited

U.S. PATENT DOCUMENTS

| | | | |
|---|---|---|---|
| 2,630,112 | 3/1953 | Zide | 126/388 |
| 3,526,891 | 9/1970 | Pope | 116/101 |
| 3,715,699 | 2/1973 | Hire | 337/376 |
| 4,165,359 | 8/1979 | Thomas et al. | 422/105 |
| 4,457,327 | 7/1984 | Pepper | 137/67 |

FOREIGN PATENT DOCUMENTS 2124895  11/1972  Fed. Rep. of Germany ... 292/DIG. 66

Primary Examiner—Charles Frankfort
Assistant Examiner—W. Morris Worth
Attorney, Agent, or Firm—Robert D. Yeager

[57] ABSTRACT

A device for indicating whether a container has been both exposed to a critical temperature and not subsequently opened which includes a housing, a temperature-sensitive member which assumes a first position and a second position within the housing, and a rigid member connected to the temperature sensitive member which moves into view when the temperature sensitive member assumes its second position upon exposure to a critical temperature, and moves out of view when the container is opened.

3 Claims, 5 Drawing Figures

TEMPERATURE SENSITIVE RECLOSURE INDICATOR

BACKGROUND OF THE INVENTION

1. Field of the Invention

The present invention relates to tamperproof reclosure indicators and more particularly to temperature sensitive reclosure indicators.

2. Description of the Prior Art

In handling sensitive materials it is often important to know both that a critical temperature has been reached and that the container holding the materials has not been tampered with. Sterilization containers, for example, must be exposed to a critical temperature to ensure the proper sterilization of the contents. In addition it is important to ascertain whether properly sterilized items within the container have been subsequently contaminated by exposure to a nonsterile environment.

Conventional sterilization container systems enploy temperature or chemical-sensitive sterility indicators. Several single use metal and plastic closure devices which are destroyed when the container is opened are available. One system is equipped with a one-way valve which maintains a vacuum in the container until the container is opened.

Temperature sensitive bimetallic discs or strips are available for a variety of uses to indicate whether goods have been exposed to a critical temperature. This type of indicator does not, however, indicate alterations in the condition of the container holding the goods apart from further temperature changes.

Accordingly, there is a need for a device which indicates that a container has been both exposed to a critical temperature and not subsequently opened. Furthermore, there is a need for such an indicator which is reusable and inexpensive.

SUMMARY OF THE INVENTION

The present invention provides a container that indicates whether the container which has been exposed to a critical temperature has subsequently been opened. Preferably, the container includes an indicator so associated with the container that the indicator moves into view when exposed to a predetermined temperature and moves out of view when the container is opened. The indicator preferably moves into view only when exposed to a predetermined temperature.

The device may include a housing which is attached to the container and which has an opening. It also may include an indicator disposed within the housing and so associated with the container that the indicator visibly engages the container only when exposed to a predetermined temperature and visibly disengages the container when the container is opened. The indicator may so engage the container when exposed to a predetermined temperature that the indicator latches the container in a closed position. The indicator may further include a temperature sensitive member, preferably a bimetallic disc or strip, which moves, preferably with a snap action, from a first position to a second position when exposed to a predetermined temperature. Either the temperature sensitive member itself or a rigid member which extends from the temperature sensitive member may move through the opening in the housing into engagement with the container, preferably the container lid or latch, when the temperature sensitive member is in the second position and may move into the housing out of engagement with the container when the container lid or latch is opened. The rigid member thereby forces the temperature sensitive member into the first position.

BRIEF DESCRIPTION OF THE DRAWINGS

The following detailed description of the preferred embodiment can be better understood if reference is made to the attached drawings in which.

DETAILED DESCRIPTION OF THE PREFERRED EMBODIMENT

Figure 5:
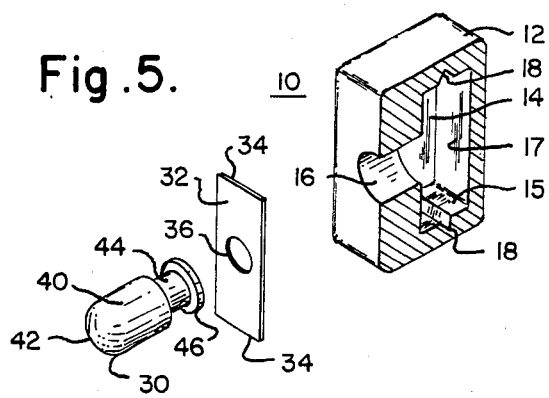
FIG. 5 is an exploded view of the indicator assembly partially in section.

The present invention, as illustrated in FIGS. 1 through 5, is a container 20 including an indicator assembly 10 for indicating whether container 20 has been both exposed to a critical temperature and not subsequently opened. Container 20 includes receptacle 21 that holds articles, and a closure 22. Receptacle 21 and closure 22 can be moved relative to each other to open and close container 20. Assembly 10 is attached by any suitable known means to the other surface of container 20, preferably in association with the latch 24 or the closure 22 of container 20.

Figure 1:
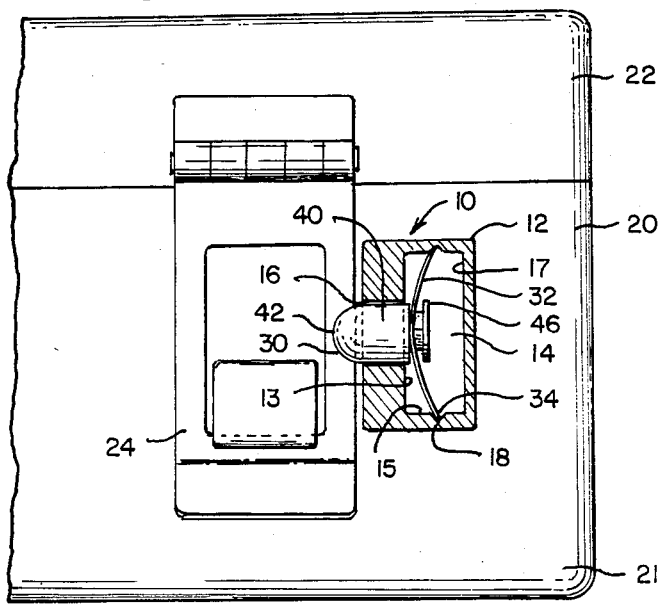
FIG. 1 is a section view of a container constructed according to the provisions of the present invention showing the temperature sensitive member of the indicator assembly in its second position.

FIG. 1 illustrates the preferred embodiment of the present invention in which the assembly 10 is in association with latch 24 of container 20. Although not illustrated, it should be appreciated that the assembly 10 may be associated with the closure 22 of container 20 without exceeding the scope of the present invention.

Referring to FIG. 1, assembly 10 includes housing 12 and indicator 30. Housing 12 has cavity 14 which has a front wall 13, through which there is an opening 16, a back wall 17 and side walls 15. A groove 18 is cut into each side wall 15. Indicator 30 includes a temperature sensitive member 32, which is illustrated as a strip but may alternatively be a disc and rigid member 40. Temperature sensitive member 32, preferably a bimetallic member, has ends 34 and a hole 36. The rigid member 40 has a head portion 42 which preferably has a semispherical end, a neck 44 and a flange 46.

Figure 3:
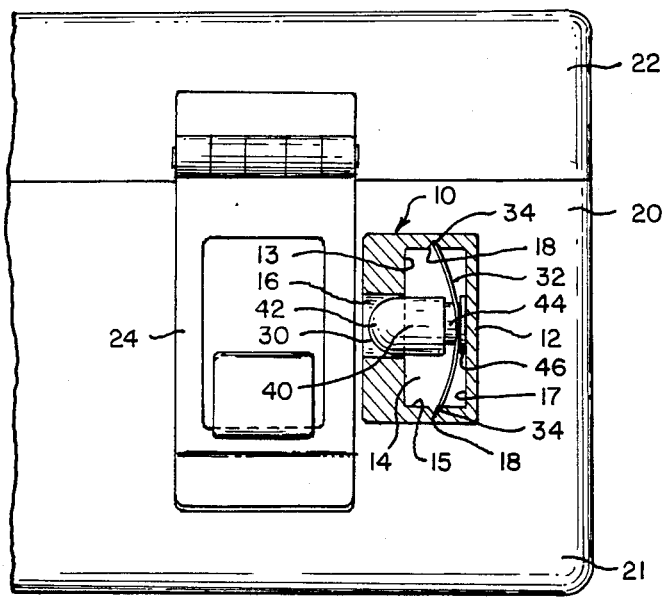
FIG. 3 is a section view of the container shown in FIG. 1 showing the temperature sensitive member in its first position.

The indicator 30 is disposed partially within cavity 14 of housing 12. Neck 44 of rigid member 40 passes through hole 36 of temperature sensitive member 32. Flange 46 is disposed toward back wall 17 of cavity 14. Head 42 is disposed toward front wall 13 and opening 16. Each end 34 of temperature sensitive member 32 rests in a groove 18 of side wall 15. The length of temperature sensitive member 32 is greater than the distance between the innermost recess of grooves 18, thus forcing temperature sensitive member 32 to assume either a concave or a convex shape with respect to front wall 13 and opening 16, as illustrated in FIGS. 1 and 3. Alternatively, the temperature sensitive member 32 may be preformed in a curved configuration which would reverse upon exposure to a critical temperature and which would not return to its first configuration without the application of the force supplied by opening the latch 24.

In operation, temperature sensitive member 32 has two positions. FIG. 3 shows assembly 10 of the present invention ready for use when the temperature sensitive member 32 is in a first position, concave with respect to front wall 13 and opening 16. The rigid member 40 is retracted within housing 12 and is not in engagement with the latch 24 of the container 20. Flange 46 rests against back wall 17 of cavity 14. Head portion 42 is completely in housing 12 in opening 16.

Figure 2:
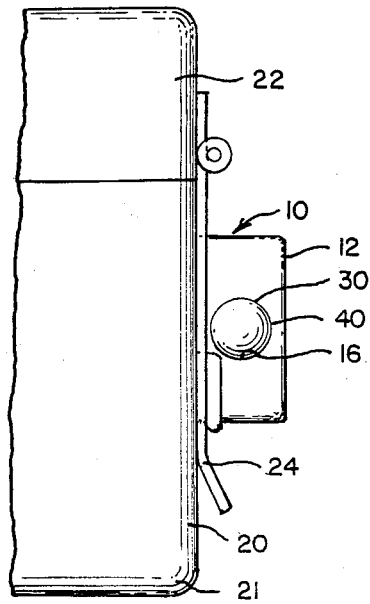
FIG. 2 is a side elevation view of the container shown in FIG. 1.

When the container 20 to which assembly 10 is attached has been exposed to a predetermined critical temperature, such as that necessary for successful sterilization, the bimetallic temperature sensitive member 32 moves, preferably with a snap action, into a second position, convex with respect to front wall 13 and opening 16. Rigid member 40 extends through opening 16 and over the face of latch 24, as illustrated in FIGS. 1 and 2.

Figure 4:
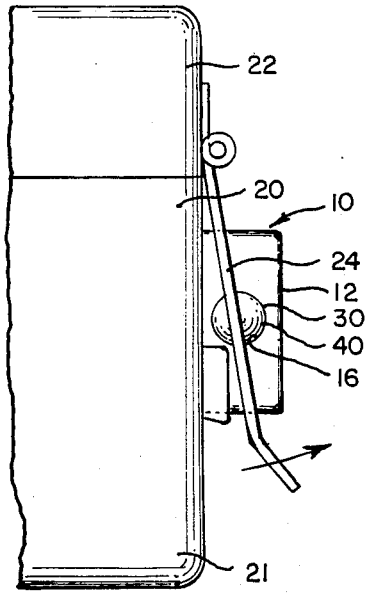
FIG. 4 is a side elevation view of the device in FIG. 3.

When the latch 24 is opened, as illustrated in FIG. 4, the latch 24 slides over the semi-spherical end of head portion 42, pushing the rigid member 40 back through opening 16 into housing 12. Rigid member 40 pushes temperature sensitive member 32 into the first position, as illustrated in FIG. 3. Rigid member 40 is not in engagement with latch 24. The rigid member 40 can move to its second position only upon reexposure to the critical temperature. Thus, a visible rigid member 40 indicates both that the container 20 to which assembly 10 is attached has been exposed to a critical temperature and has not subsequently been opened. When the rigid member 40 is retracted, the container either has not been exposed to the desired temperature or has been so exposed but has been subsequently opened. Housing 12 and the shape of head portion 42 protect assembly 10 from being tampered with. Thus, if the latch 24 is opened and the indicator 30 is retracted within housing 12, rigid member 40 cannot be pulled out of housing 12.

It should be appreciated that housing 12, rigid member 40 and temperature sensitive member 32 may assume different shapes than those illustrated in FIGS. 1 through 5 without exceeding the scope of the claimed invention.

In an alternative embodiment, the temperature sensitive member 32 may itself be adapted to move from the first position to the second position through the opening 16 in housing 12 into engagement with the container 20 upon exposure to a predetermined temperature. Opening container 20 would force the temperature sensitive member 32 back into housing 12 out of engagement with the container 20 and into the first position.

A further modification of assembly 10 would permit the indicator 30 to latch the container 20 in a closed position upon exposure to a predetermined temperature in addition to its indicator function as described above.

What is claimed is:

1. Apparatus in which articles can be sterilized and stored in a sterile condition comprising:
    a container including a receptacle for holding the articles and a closure for said receptacle, said closure and said receptacle being movable, relative to each other, between an opened position, in which microbial life can enter said container and contact the articles, and a closed position, in which said closure and said receptacle prevent entry of microbial life into said container; and
    an indicator assembly secured to said container, said indicator assembly including an indicator movable between two positions that are visually distinguishable from each other at least when the receptacle and closure assume their closed position, said indicator assembly including a temperature sensitive element, said element being so mounted to said indicator assembly that exposure of said element to an environment at a temperature falling within a predetermined range of temperatures for at least a predetermined length of time, when said indicator is in a first of its said positions, causes said element to move said indicator to a second of its said positions, subsequent exposure of said element to an environment at a temperature falling ouside said predetemined temperature range being insufficient to cause said element to return said indicator to its said first position, subseqent exposure of said element to an environment as a temperature not falling within said predetermined temperature range for at least a predetermined period of time coupled with the exertion of a force against said indicator sufficient to cause said indicator to travel through at least a predetermined distance toward its said first position causing said indicator to assume its said first position and to remain in said first position after said force is removed from said indicator;
    said container including means for exerting said force against said indicator to move said indicator through said predetermined distance each time said indicator is in its said second position and said closure and container are moved, relative to each other, from a said closed position to a said opened position.

2. The apparatus recited by claim 1 wherein said indicator assembly permits relative movement of said receptacle and said closure from their said closed position to their said opened position regardless of the said position assumed by said indicator and the positioning of said element during use of said container.

3. Apparatus in which articles can be sterilized and stored in a sterile condition comprising:
    a container including a receptacle for holding the articles and a closure for said receptacle, said closure and said receptacle being movable, relative to each other, between an opened position, in which microbial life can enter said container and contact the articles, and a closed position, in which said closure and said receptacle prevent entry of microbial life into said container;
    a latch mounted to said container for securing said receptacle and said closure in a said closed position; and
    an indicator assembly secured to said container including a housing, said indicator assembly further including an indicator movable between two positions that are visually distinguishable from each other at least when said receptacle and said closure assume their closed position, said indicator assembly including a temperature sensitive bimetallic strip secured at its ends to said housing, the distance between the points at which said ends of said strip are mounted being less than the length of said strip to cause said strip to be bowed, said indicator being secured to said strip and moving with the bowed section of said strip, said strip bowing in a first direction to move said indicator from a first to a second of its said positions when said strip is exposed to an environment at a temperature falling within a predetermined range for at least a predetermined period of time, subsequent exposure of said strip to an environment at a temperature outside said range being insufficient to cause said strip to bow in a second direction to return said indicator to its said first position, subsequent movement of said indicator to its said first position being effected by exposing said indicator to an environment at a temperature outside said range for at least a predetermined period of time and exerting a force against said indicator that causes said strip to bow in said second direction and move said indicator to its said first position;

said indicator assembly being so mounted to said container that movement of said latch, when said indicator is in its said second position and said strip has been exposed to an environment at a temperature falling outside said range for at least a predetermined period of time, to a position that permits movement of said closure and said container to a said opened position exerts said force on said indicator to return said indicator to its said first position;

said indicator assembly permitting relative movement of said receptacle and said closure from their said closed position to their said opened position regardless of the said position assumed by said indicator and the positioning of said strip during use of said container.

* * * * *

UNITED STATES PATENT AND TRADEMARK OFFICE
CERTIFICATE OF CORRECTION

PATENT NO. : 4,539,929

DATED : September 10, 1985

INVENTOR(S) : Joseph T. Sestak and Dennis C. Coon

It is certified that error appears in the above—identified patent and that said Letters Patent is hereby corrected as shown below:

Col. 2, line 19, delete "device" and substitute therefor --container shown--; and Col. 2, line 35, delete "other" and substitute therefor --outer--.

Signed and Sealed this

Twenty-sixth Day of November 1985

[SEAL]

Attest:

DONALD J. QUIGG

Attesting Officer

Commissioner of Patents and Trademarks